(12) United States Patent
Santini, Jr. et al.

(10) Patent No.: US 7,537,590 B2
(45) Date of Patent: May 26, 2009

(54) MULTI-RESERVOIR DEVICE FOR TRANSDERMAL DRUG DELIVERY AND SENSING

(75) Inventors: John T. Santini, Jr., Chelmsford, MA (US); Mark A. Staples, Cambridge, MA (US); Stephen J. Herman, Andover, MA (US)

(73) Assignee: MicroCHIPS, Inc., Bedford, MA (US)

( * ) Notice: Subject to any disclaimer, the term of this patent is extended or adjusted under 35 U.S.C. 154(b) by 554 days.

(21) Appl. No.: 11/194,157

(22) Filed: Aug. 1, 2005

(65) Prior Publication Data

US 2006/0024358 A1 Feb. 2, 2006

Related U.S. Application Data

(60) Provisional application No. 60/592,537, filed on Jul. 30, 2004.

(51) Int. Cl.
*A61K 9/22* (2006.01)
(52) U.S. Cl. .................................. 604/890.1
(58) Field of Classification Search ............ 604/20, 604/48, 306, 307, 890.1; 424/448
See application file for complete search history.

(56) References Cited

U.S. PATENT DOCUMENTS

| | | | |
|---|---|---|---|
| 3,692,027 A | 9/1972 | Ellinwood, Jr. | |
| 3,952,741 A | 4/1976 | Baker | |
| 3,964,482 A * | 6/1976 | Gerstel et al. | 604/890.1 |
| 4,003,379 A | 1/1977 | Ellinwood, Jr. | |
| 4,146,029 A | 3/1979 | Ellinwood, Jr. | |
| 4,360,019 A | 11/1982 | Portner et al. | |
| 4,507,115 A | 3/1985 | Kambara et al. | |
| 4,585,652 A | 4/1986 | Miller et al. | |
| 4,731,049 A | 3/1988 | Parsi | |
| 4,731,051 A | 3/1988 | Fischell | |
| 4,793,825 A | 12/1988 | Benjamin et al. | |

(Continued)

FOREIGN PATENT DOCUMENTS

DE 197 16 683 C1 6/1998

(Continued)

OTHER PUBLICATIONS

Reynaerts, et al., "An implantable drug-delivery system based on shape memory alloy micro-actuation," *Sensors and Actuators* A 61: 455-462 (1997).

*Primary Examiner*—Nicholas D Lucchesi
*Assistant Examiner*—Victoria P Campbell
(74) *Attorney, Agent, or Firm*—Sutherland Asbill & Brennan LLP

(57) ABSTRACT

Devices and methods are provided for transdermal administration of a pharmaceutical agent to a patient in need thereof. The device includes a substrate, a plurality of discrete reservoirs in the substrate, one or more pharmaceutical agents stored in the reservoirs, discrete reservoir caps that prevent the pharmaceutical agent from passing out from the reservoirs until desired, control means for actuating release of the one or more pharmaceutical agents from one or more of the reservoirs by disintegrating or permeabilizing the reservoir caps, means for securing the device to the skin of the patient, and means for transporting the pharmaceutical agent to the skin following release from the one or more of the reservoirs. In another embodiment, the device is adapted for diagnostic sensing instead of or in addition to drug delivery.

30 Claims, 6 Drawing Sheets

U.S. PATENT DOCUMENTS

| | | | |
|---|---|---|---|
| 4,994,023 | A | 2/1991 | Wllinghoff et al. |
| 5,041,107 | A | 8/1991 | Heil, Jr. |
| 5,042,975 | A | 8/1991 | Chien et al. |
| 5,147,297 | A | 9/1992 | Myers et al. |
| 5,167,625 | A | 12/1992 | Jacobsen et al. |
| 5,170,801 | A | 12/1992 | Casper et al. |
| 5,196,002 | A | 3/1993 | Hanover et al. |
| 5,200,051 | A | 4/1993 | Cozzette et al. |
| 5,202,018 | A | 4/1993 | Horanyl et al. |
| 5,252,294 | A | 10/1993 | Kroy et al. |
| 5,254,081 | A | 10/1993 | Maurer et al. |
| 5,279,607 | A | 1/1994 | Schentag et al. |
| 5,288,504 | A | 2/1994 | Versic |
| 5,318,557 | A | 6/1994 | Gross |
| 5,336,213 | A | 8/1994 | D'Angelo et al. |
| 5,366,454 | A | 11/1994 | Currie et al. |
| 5,368,588 | A | 11/1994 | Bettinger et al. |
| 5,368,704 | A | 11/1994 | Madou et al. |
| 5,387,419 | A | 2/1995 | Levy et al. |
| 5,427,585 | A | 6/1995 | Bettinger et al. |
| 5,429,822 | A | 7/1995 | Gresser et al. |
| 5,443,508 | A | 8/1995 | Giampapa |
| 5,474,527 | A | 12/1995 | Bettinger et al. |
| 5,490,962 | A | 2/1996 | Cima et al. |
| 5,533,995 | A | 7/1996 | Corish et al. |
| 5,585,069 | A | 12/1996 | Zanzucchi et al. |
| 5,605,662 | A | 2/1997 | Heller et al. |
| 5,782,799 | A | 7/1998 | Jacobsen et al. |
| 5,797,898 | A | 8/1998 | Santini, Jr. et al. |
| 5,824,204 | A | 10/1998 | Jerman |
| 5,842,787 | A | 12/1998 | Kopf-Sill et al. |
| 5,843,767 | A | 12/1998 | Beattie |
| 5,860,957 | A | 1/1999 | Jacobsen et al. |
| 5,925,069 | A | 7/1999 | Graves et al. |
| 5,957,579 | A | 9/1999 | Kopf-Sill et al. |
| 5,972,027 | A | 10/1999 | Johnson |
| 5,976,101 | A | 11/1999 | Sibalis |
| 5,989,445 | A | 11/1999 | Wise et al. |
| 6,001,090 | A | 12/1999 | Lenhart |
| 6,066,163 | A | 5/2000 | John |
| 6,068,752 | A | 5/2000 | Dubrow et al. |
| 6,083,763 | A | 7/2000 | Balch |
| 6,096,656 | A | 8/2000 | Matzke et al. |
| 6,114,658 | A | 9/2000 | Roth et al. |
| 6,123,861 | A | 9/2000 | Santini, Jr. et al. |
| 6,171,850 | B1 | 1/2001 | Nagle et al. |
| 6,219,574 | B1 | 4/2001 | Cormier et al. |
| 6,230,051 | B1 | 5/2001 | Cormier et al. |
| 6,232,150 | B1 | 5/2001 | Lin et al. |
| 6,243,608 | B1 | 6/2001 | Pauly et al. |
| 6,261,584 | B1 | 7/2001 | Peery et al. |
| 6,264,990 | B1 | 7/2001 | Knepp et al. |
| 6,306,420 | B1 | 10/2001 | Cheikh |
| 6,334,856 | B1 | 1/2002 | Prausnitz et al. |
| 6,349,232 | B1 | 2/2002 | Gordon |
| 6,366,794 | B1 | 4/2002 | Moussy et al. |
| 6,377,847 | B1 | 4/2002 | Keusch |
| 6,488,959 | B2 | 12/2002 | Stanley |
| 6,491,657 | B2 | 12/2002 | Rowe |
| 6,491,666 | B1 | 12/2002 | Santini, Jr. et al. |
| 6,497,729 | B1 | 12/2002 | Moussy et al. |
| 6,503,231 | B1 | 1/2003 | Prausnitz et al. |
| 6,517,864 | B1 * | 2/2003 | Orup Jacobsen et al. .... 424/449 |
| 6,527,762 | B1 | 3/2003 | Santini, Jr. et al. |
| 6,537,250 | B1 | 3/2003 | Kiresel |
| 6,537,256 | B2 | 3/2003 | Santini, Jr. et al. |
| 6,551,838 | B2 | 4/2003 | Santini, Jr. et al. |
| 6,558,321 | B1 | 5/2003 | Burd et al. |
| 6,571,125 | B2 | 5/2003 | Thompson |
| 6,620,123 | B1 | 9/2003 | Mitragotri |
| 6,629,968 | B1 | 10/2003 | Jain et al. |
| 6,632,606 | B1 | 10/2003 | Ullman |
| 6,656,162 | B2 | 12/2003 | Santini, Jr. et al. |
| 6,661,707 | B2 | 12/2003 | Choi et al. |
| 6,663,615 | B1 | 12/2003 | Madou et al. |
| 6,669,683 | B2 | 12/2003 | Santini, Jr. et al. |
| 6,676,363 | B1 | 1/2004 | Solignac |
| 6,702,857 | B2 | 3/2004 | Brauker et al. |
| 6,723,077 | B2 | 4/2004 | Pickup et al. |
| 6,730,072 | B2 | 5/2004 | Schawgo et al. |
| 6,741,877 | B1 | 5/2004 | Shults et al. |
| 6,743,211 | B1 | 6/2004 | Prausnitz et al. |
| 6,756,053 | B2 | 6/2004 | Zhang |
| 6,773,429 | B2 | 8/2004 | Sheppard, Jr. et al. |
| 6,808,522 | B2 | 10/2004 | Richards et al. |
| 6,827,250 | B2 | 12/2004 | Uhland et al. |
| 6,849,463 | B2 | 2/2005 | Santini, Jr. et al. |
| 6,875,208 | B2 | 4/2005 | Santini, Jr. et al. |
| 7,004,928 | B2 | 2/2006 | Aceti et al. |
| 2001/0056255 | A1 | 12/2001 | Kost |
| 2002/0022826 | A1 | 2/2002 | Reynolds et al. |
| 2002/0072784 | A1 | 6/2002 | Sheppard, Jr. et al. |
| 2002/0082527 | A1 | 6/2002 | Liu |
| 2002/0099359 | A1 | 7/2002 | Santini, Jr. et al. |
| 2002/0119176 | A1 | 8/2002 | Greenberg et al. |
| 2002/0161352 | A1 | 10/2002 | Lin et al. |
| 2002/0187260 | A1 | 12/2002 | Sheppard, Jr. et al. |
| 2003/0069560 | A1 | 4/2003 | Adamis et al. |
| 2003/0105455 | A1 | 6/2003 | Santini, Jr. et al. |
| 2003/0176854 | A1 | 9/2003 | Rodstrom |
| 2004/0043042 | A1 | 3/2004 | Johnson et al. |
| 2004/0082937 | A1 | 4/2004 | Ausiello et al. |
| 2004/0106904 | A1 | 6/2004 | Gonnelli et al. |
| 2004/0106914 | A1 | 6/2004 | Coppeta et al. |
| 2004/0106953 | A1 | 6/2004 | Yomtov et al. |
| 2004/0121486 | A1 * | 6/2004 | Uhland et al. ............... 436/174 |
| 2004/0127942 | A1 | 7/2004 | Yomtov et al. |
| 2004/0166140 | A1 | 8/2004 | Santini, Jr. et al. |
| 2004/0247671 | A1 | 12/2004 | Prescott et al. |
| 2005/0050859 | A1 | 3/2005 | Coppeta et al. |
| 2005/0055014 | A1 | 3/2005 | Coppeta et al. |
| 2005/0077584 | A1 | 4/2005 | Polito et al. |
| 2005/0096587 | A1 | 5/2005 | Santini, Jr. et al. |
| 2005/0100937 | A1 | 5/2005 | Holmes |
| 2005/0143715 | A1 | 6/2005 | Santini, Jr. et al. |
| 2006/0283465 | A1 | 12/2006 | Nickel et al. |
| 2007/0260201 | A1 | 11/2007 | Prausnitz et al. |

FOREIGN PATENT DOCUMENTS

| | | |
|---|---|---|
| JP | 58135808 A | 8/1983 |
| WO | WO 93/03790 A1 | 3/1993 |
| WO | WO 99/03684 A2 | 3/1993 |
| WO | WO 98/26814 A1 | 6/1998 |
| WO | WO 01/28629 A1 | 4/2001 |
| WO | WO 01/37926 A1 | 5/2001 |
| WO | WO 01/88525 A1 | 5/2001 |
| WO | WO 02/056862 A2 | 7/2002 |
| WO | WO 02/058678 A2 | 8/2002 |
| WO | WO 03/024355 A1 | 3/2003 |
| WO | 2006060106 A1 | 6/2006 |

* cited by examiner

MULTI-RESERVOIR DEVICE FOR TRANSDERMAL DRUG DELIVERY AND SENSING

CROSS-REFERENCE TO RELATED APPLICATIONS

This application claims the benefit of U.S. Provisional Application No. 60/592,537, filed Jul. 30, 2004. The application is incorporated herein by reference.

BACKGROUND OF THE INVENTION

This invention is generally in the field of devices and methods for the transdermal drug delivery and analyte sensing.

Transdermal drug delivery systems generally rely on diffusion of drug across the skin. In a typical conventional technology, the transdermal drug delivery system is in the form of a multi-layered patch that includes a backing or cover layer, a drug matrix/reservoir, a diffusion control membrane, and an adhesive layer for attaching the system to the surface of the skin. Examples of drugs delivered with such systems include scopolamine (Trasderm-Scop™), nicotine, nitroglycerin (Nitro-Dur™), estradiol (Estraderm™), and testosterone. However, transdermal patches generally are unsuitable for delivery of macromolecules. Others have sought to improve transdermal delivery of drug molecules, particularly where the size and hydrophilicity of the drug molecules significantly hinders diffusion through the stratum corneum, over that obtained with passive diffusion alone, by including with the transdermal drug delivery systems an active mechanism, such as iontophoresis, electroporation, ultrasound, or heat, or by disrupting the stratum corneum with microneedles or the like.

In transdermal and other drug delivery systems, it is generally desirable to store and protect the drug formulation until the time it is to be delivered to a patient, because exposure to environmental components (e.g., oxygen, humidity) may damage or prematurely degrade the pharmaceutical agent. However, in various conventional transdermal drug delivery systems which contain several days worth of doses of the drug, the entire drug formulation is contained in a single reservoir, such that is it not possible to protect or isolate individual doses. It would be desirable to be able to do so, particularly for relatively fragile pharmaceutical agent molecules.

In addition, with a conventional patch-type drug delivery system, it generally is not possible to change or fine-tune the rate of administration of drug once the patch is applied to the patient. It would be desirable to provide new and improved methods and devices for the controlled delivery of one or more drugs to a patient by transdermal administration. For example, it would be advantageous to be able to store and transdermally administer multiple discrete doses of a drug formulation, using a device which the physician can easily vary or fine tune the time and rate of drug administration.

SUMMARY OF THE INVENTION

Devices and methods have been developed for transdermal administration of one or more pharmaceutical agents to a patient in need thereof. In one aspect, the device includes a substrate, a plurality of discrete reservoirs in the substrate, one or more pharmaceutical agents stored in the reservoirs, discrete reservoir caps that prevent the pharmaceutical agent from passing out from the reservoirs, control means for actuating release of the pharmaceutical agent from one or more of the reservoirs by disintegrating or permeabilizing the reservoir caps, means for securing the device to the skin of the patient, and means for transporting to the skin the one or more pharmaceutical agents following release from the one or more of the reservoir. In one embodiment, the device includes a housing which contains the substrate, reservoirs, control means, and a power source. In one embodiment, the device further includes a removably attachable electronics portion which comprises the power source and at least a portion of the control means.

In one embodiment, the reservoir cap is formed of an electrically conductive material and the control means comprises an electrical input lead connected to said reservoir cap, an electrical output lead connected to said reservoir cap, wherein the reservoir cap is disintegrated by application of an electrical current through the reservoir cap via the input lead and output lead. The device may further include a source of electric power, such as a battery or capacitor, for applying the electrical current.

In one embodiment, the reservoirs are microreservoirs. In one embodiment, the reservoir cap comprises a metal film.

In one embodiment, the means for securing the device comprises a pressure sensitive adhesive. In one embodiment, the means for securing comprises an adhesive layer that is permeable to the pharmaceutical agent or analyte.

In one embodiment, the means for transporting includes a transport medium disposed between the reservoir caps and the skin. For example, the transport medium can include a permeable body through which the pharmaceutical agent released from the reservoirs can diffuse. In one embodiment, the transport medium comprises a reservoir containing a liquid, gel, or semi-solid permeation material. In another embodiment, the means for transporting comprises a plurality of microneedles. In still another embodiment, the means for transporting comprises one or more chemical penetration enhancers. In various embodiments, the means for transporting comprises means for effecting iontophoresis, electroosmosis, or electroporation. In one embodiment, the means for transporting comprises an ultrasound generator. In a further embodiment, the means for transporting comprises a heating element. In one embodiment, the means for transporting comprises a flexible or rigid member having media-filled holes with spacing corresponding to reservoir membrane openings, which allows release of reservoir contents without dilution.

In various specific embodiments, the one or more pharmaceutical agents include a drug selected from among androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, anti-obesity agents, nicotine, testosterone, estradiol, nitroglycerin, clonidine, dexamethasone, wintergreen oil, tetracaine, lidocaine, fentanyl, sufentanil, progestrone, insulin, Vitamin A, Vitamin C, Vitamin E, prilocaine, bupivacaine, sumatriptan, dihydroergotamine, and combinations thereof.

In another aspect, a medical device is provided for transdermal administration of one or more pharmaceutical agents to a patient in need thereof, which includes a substrate, a plurality of discrete reservoirs in the substrate, one or more pharmaceutical agents stored in the reservoirs, discrete reservoir caps which prevent the one or more pharmaceutical agents from passing out from the reservoirs, control means for actuating release of the one or more pharmaceutical agents from one or more of the reservoirs by disintegrating or permeabilizing the reservoir caps, an adhesive or strap material for securing the device to the skin of the patient, and a body defining a transport medium reservoir disposed between the reservoir caps and the skin of the patient, the body and reservoir facilitating transport of the pharmaceutical agent to the skin following its release from one or more of the reservoir. In one embodiment, the transport medium reservoir contains a liquid, gel, or semi-solid permeation material. In one embodiment, the transport medium reservoir comprises a single pool of a biocompatible transport fluid into which the pharmaceutical agent is diluted prior to delivery to the skin. In another embodiments the transport medium reservoir comprises individual channels for delivery of the pharmaceutical agent with no or minimal dilution prior to delivery to the skin.

In another aspect, a device is provided for sensing an analyte in a human or other animal. In one embodiment, the device includes a substrate; a plurality of discrete reservoirs in the substrate, the reservoirs having at least one opening; one or more sensors or diagnostic agents stored in the reservoirs; discrete reservoir caps which cover said at least one opening; control means for disintegrating or permeabilizing the reservoir caps; means for securing the device to the skin of the patient; and means for transporting an analyte from the skin to the one or more sensors or for transporting the one or more diagnostic agents to the skin following release of said diagnostic agents from the one or more of the reservoir.

DETAILED DESCRIPTION OF THE INVENTION

Figure 1:
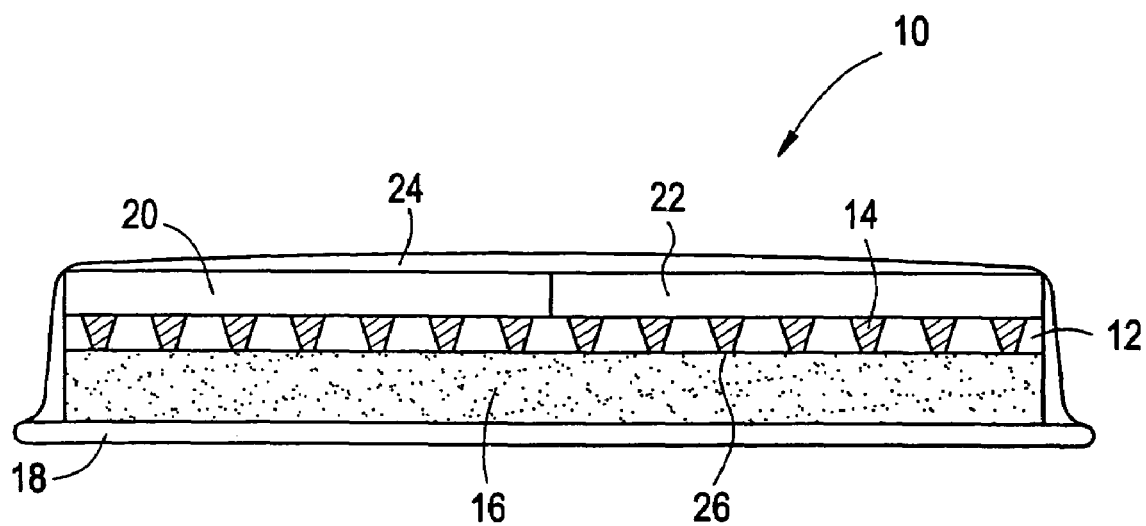
FIG. 1 is a cross-sectional view of one embodiment of the medical device for transdermal drug delivery or analyte sensing described herein.

Medical devices have been developed for the transdermal administration of one or more pharmaceutical agents to patient in need thereof, or for analyte sensing/diagnostics. In a preferred embodiment, the devices isolate each dose or portions of a dose of the pharmaceutical agent within multiple individual (discrete) reservoirs, which typically are arrayed in/across a body portion of the device. Advantageously, the isolated doses or partial doses are protected from environmental components that may damage or prematurely degrade the pharmaceutical agent or other reservoir contents, until the desired time for release or exposure of the pharmaceutical agent or other reservoir contents.

As used herein, the terms "comprise," "comprising," "include," and "including" are intended to be open, non-limiting terms, unless the contrary is expressly indicated.

The Medical Device

In one aspect, the device comprises a substrate; a plurality of discrete reservoirs in the substrate; one or more pharmaceutical agents stored in the reservoirs; discrete reservoir caps that prevent the one or more pharmaceutical agents from passing out from the reservoirs; control means for actuating release of the pharmaceutical agents from one or more of the reservoirs by disintegrating or permeabilizing the reservoir caps; means for securing the device to the skin of the patient; and means for transporting the pharmaceutical agent to the skin following release from one or more of the reservoirs.

In another aspect, the device is used to deliver a diagnostic agent into the skin. For instance, the agent could be a small molecule metabolite reporter, used in glucose detecting.

In still another aspect, the device is not used to deliver something but to contain a plurality of sensors for selective exposure. For example, the device could be adapted to sense an analyte withdrawn, either by passive or active mechanisms, from or through the skin.

Substrate/Reservoirs

The device comprises a substrate, i.e., a body portion, that includes the plurality of discrete reservoirs, e.g., in the form of a two-dimensional array of selectively spaced reservoirs—located in discrete positions—across at least one surface of the body portion. A reservoir is a well, a recess, a hole or a cavity, located in a solid structure and suitable for containing a quantity of another material and/or a secondary device.

In various embodiments, the body portion comprises silicon, a metal, a ceramic, a polymer, or a combination thereof. Examples of suitable substrate materials include metals, ceramics, semiconductors, glasses, and degradable and non-degradable polymers. In one embodiment, each reservoir is formed of hermetic materials (e.g., metals, silicon, glasses, ceramics) and is hermetically sealed by at least one reservoir cap. In one case, if the reservoir has a second opening, distal the reservoir cap-sealed opening, then a hermetic seal can be formed at that distal opening as well, in order for the reservoir contents to be hermetically isolated within the reservoir. Alternatively, where the reservoir has two opposed openings, each can be covered by a reservoir cap which can be opened for release or exposure of the reservoir contents. In still another case, a reservoir can have two or more separate openings on the same side of the reservoir, which can be covered by one or two or more discrete reservoir caps. The reservoirs can be in essentially any shape, and typically are shaped to facilitate reservoir manufacture and loading of contents, as well as packing of reservoirs into the substrate.

The substrate can have a variety of shapes, or shaped surfaces. It can, for example, have a release side (i.e., an area having reservoir caps) that is planar or curved. The substrate may, for example, be in a shape selected from circular, square, or ovoid disks. In one embodiment, the release side can be shaped to conform to a curved tissue surface.

The device body can be flexible or rigid. In one embodiment, the device flexibly conforms to a tissue surface as taught in U.S. Patent Application Publication No. 2002/0099359 to Santini et al., which is incorporated herein by reference.

The substrate may consist of only one material, or may be a composite or multi-laminate structure, that is, composed of several layers of the same or different substrate materials bonded or fused together. In one embodiment, the substrate comprises layers of silicon and Pyrex bonded together. In another embodiment, the substrate comprises multiple silicon wafers bonded together. In yet another embodiment, the substrate comprises a low-temperature co-fired ceramic (LTCC). In one embodiment, the body portion is the substrate of a microchip device. In one example, this substrate is formed of silicon.

In one embodiment, the substrate is formed from one or more polymers, copolymers, or blends thereof. For some transdermal applications, the reservoirs need not be defined/enclosed by hermetic materials, particularly where the time the reservoir contents are isolated is relatively short, for example, when the transdermal device is used only for a period of a few days (e.g., less than 2 days, less than 3 days). In such cases, polymeric substrates may be preferred, particularly because they can be less costly to manufacture than some silicon or ceramic substrate devices. In addition, the polymeric substrate can be easily made to conform to a particular skin surface area of the human or animal body.

In a preferred embodiment, the reservoirs are microreservoirs. As used herein, the term "microreservoir" refers to a discrete hole or concave-shaped space in a solid structure suitable for releasably containing a material. The structure is of a size and shape suitable for filling with a microquantity of the material, which comprises a drug. In one embodiment, the microreservoir has a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 nL, greater than about 50 nL, greater than about 1 µL, etc.). The shape and dimensions of the microreservoir can be selected to maximize or minimize contact area between the drug material and the surrounding surface of the microreservoir. As used herein, the term "microquantity" refers to small volumes between 1 nL and 500 µL. In one embodiment, the microquantity is between 1 nL and 1 µL. In another embodiment, the microquantity is between 10 nL and 500 nL.

Microreservoirs can be fabricated in a structural body portion using fabrication techniques known in the art. Representative fabrication techniques include MEMS fabrication processes or other micromachining processes, various drilling techniques (e.g., laser, mechanical, and ultrasonic drilling, electrical discharge machining (EDM)), and build-up techniques, such as LTCC (low temperature co-fired ceramics), punch- or embossing-type processes, thin film or tape processes. The surface of the microreservoir optionally can be treated or coated to alter one or more properties of the surface. Examples of such properties include hydrophilicity/hydrophobicity, wetting properties (surface energies, contact angles, etc.), surface roughness, electrical charge, release characteristics, biocompatibility, and the like. The coating material also can be selected to affect biostability or tissue interactions with the device or with the reservoir contents. Other fabrication processes, particularly ones useful with polymeric substrates, can be used, including injection molding, thermal compression molding, extrusion, embossing, solvent casting, and other polymer forming techniques known in the art. See also U.S. Patent Application Publication No. 2002/0107470 A1 to Richards, et al., which is incorporated herein by reference.

In other embodiments, the reservoirs are larger than microreservoirs and can contain a quantity of drug formulation larger than a microquantity. For example, the volume of each reservoir can be greater than 10 µL (e.g., at least 20 µL, at least 50 µL, at least 100 µL, at least 250 µL, etc.) and less than 10 mL (e.g., less than 5 mL, less than 1000 µL, less than 500 µL, less than 300 µL, etc.). These may be referred to as macro-reservoirs and macro-quantities, respectively. Unless explicitly indicated to be limited to either micro- or macro-scale volumes/quantities, the term "reservoir" is intended to include both.

Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, manufacturing limitations, and/or total device size limitations suitable for reasonably comfortable attachment to a patient's skin.

Different device thicknesses may be chosen, depending for example of the type of application. For example, in sensing/diagnostic applications, the thickness may impact analyte transport and thus sensor response. Accordingly, it may be useful to provide a relatively thin substrate for certain sensing devices. As another example, in drug delivery applications, thicker substrates may be desired in order to increase reservoir depth and volume to contain more drug formulation, enabling increased dosage loading.

The substrate has at least two, or preferably many, discrete reservoirs. In various embodiments, tens, hundreds, or thousands of reservoirs are arrayed across the substrate. For instance, the device could include between 50 and 250 reservoirs, where each reservoir contains a single dose of a drug for release, which for example could be released hourly or daily over a period of several days. Unlike a typical conventional transdermal device, the present multi-reservoir devices can readily store and delivery different drug formulations from a single device. For example, different reservoirs could contain different drugs, or different reservoirs could contain different dosages or concentrations of the same drug.

In a preferred embodiment, the device comprises a microchip chemical delivery device, as taught in U.S. Pat. No. 5,7979,898, which is incorporated herein by reference. In other embodiments, the device could include polymeric chips or devices, as well other devices containing arrays of reservoirs, composed of non-silicon based materials that might not be referred to as "microchips."

Pharmaceutical Agent/Formulation

Essentially any pharmaceutical agent, i.e., therapeutic or prophylactic agent (e.g., an active pharmaceutical ingredient or API), suitable for transdermal administration can be used with the device described herein. The present devices would be particularly useful for the storage and delivery of drugs that currently are not suitable for use with conventional transdermal systems due to instability issues associated with the drug. For example, a drug or drug formulation that is easily degradable could be protected until needed using the multiple reservoirs, each of which can be hermetically sealed until ruptured when needed to release the drug contained therein. In this way, only the quantity of the drug needed at a particular time is exposed; the remaining drug remains stored and protected. The device can deliver a single pharmaceutical agent or a combination of pharmaceutical agents, which can be stored together in the same reservoir or stored in separate reservoirs. Depending on the application, the device and formulation may be tailored to deliver the active ingredient locally or systemically.

The pharmaceutical agent (also referred to herein as a drug) can be provided in the reservoirs in a solid, liquid, semi-solid, solution, or suspension, or emulsion formulation. It can be in a pure form or combined with one or more excipient materials. As used herein, "pure form" of the drug includes the API, residual moisture, and any chemical species combined with the API in a specific molar ratio that is isolated with the API during preparation of the API (for instance, a counter-ion) and which has not been added as an excipient.

In one embodiment, the drug is formulated in a matrix form, comprising a matrix material in which the drug is contained or dispersed. The matrix material further controls release of the drug by controlling dissolution and/or diffusion of the drug from the reservoir, and may enhance stability of the drug molecule while stored in the reservoir.

In one embodiment, the drug is formulated with an excipient material that is useful for accelerating release, e.g., a water-swellable material that can aid in pushing the drug out of the reservoir and through any tissue capsule over the reservoir. Examples include hydrogels and osmotic pressure generating agents known in the art.

In another embodiment, the drug is formulated with a penetration enhancer(s). The penetration enhancer(s) further controls release of the drug by facilitating transport of the drug across the skin into the local administration site or systemic delivery.

Pharmaceutical Agent

The drug can comprise small molecules, large (i.e., macro-) molecules, or a combination thereof. In one embodiment, the large molecule drug is a protein or a peptide. In various other embodiments, the drug can be selected from amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants (e.g., LMWH, pentasaccharides), antibiotics (e.g., immunosuppressants), analgesic agents, and vitamins.

In one embodiment, the drug is a protein. Examples of suitable types of proteins include glycoproteins, enzymes (e.g., proteolytic enzymes), hormones or other analogs (e.g., LHRH, steroids, corticosteroids, growth factors), antibodies (e.g., anti-VEGF antibodies, tumor necrosis factor inhibitors), cytokines (e.g., $\alpha$-, $\beta$-, or $\gamma$-interferons), interleukins (e.g., IL-2, IL-10), and diabetes/obesity-related therapeutics (e.g., insulin, exenatide, PYY, GLP-1 and its analogs). In one embodiment, the drug is a gonadotropin-releasing (LHRH) hormone analog, such as leuprolide. In another exemplary embodiment, the drug comprises parathyroid hormone, such as a human parathyroid hormone or its analogs, e.g., hPTH (1-84) or hPTH(1-34). In a further embodiment, the drug is selected from nucleosides, nucleotides, and analogs and conjugates thereof. In yet another embodiment, the drug comprises a peptide with natriuretic activity, such as atrial natriuretic peptide (ANP), B-type (or brain) natriuretic peptide (BNP), C-type natriuretic peptide (CNP), or dendroaspis natriuretic peptide (DNP). In still another embodiment, the drug is selected from diuretics, vasodilators, inotropic agents, anti-arrhythmic agents, $Ca^+$ channel blocking agents, anti-adrenergics/sympatholytics, and renin angiotensin system antagonists. In one embodiment, the drug is a VEGF inhibitor, VEGF antibody, VEGF antibody fragment, or another anti-angiogenic agent. Examples include an aptamer, such as MACUGEN™ (Pfizer/Eyetech) (pegaptanib sodium)) or LUCENTIS™ (Genetech/Novartis) (rhuFab VEGF, or ranibizumab), which could be used in the prevention of choroidal neovascularization. In yet a further embodiment, the drug is a prostaglandin, a prostacyclin, or another drug effective in the treatment of peripheral vascular disease.

In one embodiment, the device delivers one or more drugs known in the art for use in pain management. Examples include lidocaine and fentanyl. In a further embodiment, the drug is an anti-inflammatory, such as dexamethasone.

In another embodiment, the drug is an anti-emetic, such as a 5HT-5 antagonist. In yet another embodiment, the drug is a NSAID, such as ketaprofen. In another embodiment, the drug is an anti-anxiety drug, such as benzodiazepines. In still another embodiment, the drug is a dipeptidyl peptidase 4 inhibitor (DPP-4 inhibitor). In a further embodiment, the drug is an anticoagulant, such as warfarin, heparin, LMWH, oligoasaccharides such as idraparinux and fondaparinux, and ximelagatran. In still another embodiment, the drug is an angiogenic agent, such as VEGF. In one embodiment, a device includes both angiogenic agents and anti-inflammatory agents. In various embodiments, the drug is a bone morphogenic protein, a growth factor, or a growth or differentiation factor.

The reservoirs in one device can include a single drug or a combination of two or more drugs, and can further include one or more pharmaceutically acceptable carriers. Two or more can be stored together and released from the same one or more reservoirs or they can each be stored in and released from different reservoirs.

The device is useful to delivery a variety of drugs, either passively or with the aid of some acceleration means. For example, oligonucleotide drugs may be delivered with the aid of iontophoresis or electroporation.

Drugs that may be delivered using the devices and methods described herein include those listed in Table 1 below.

TABLE 1

Transdermal Drug Delivery Compounds

| Existing Drug Name | Current Delivery Mechanism(s) | Notes |
|---|---|---|
| Clonidine | Passive | Marketed |
| Estradiol | Passive | Marketed |
| Fentanyl | Passive, Iontophoresis | Marketed |
| Nicotine | Passive | Marketed |
| Nitroglycerin | Passive | Marketed |
| Scopolamine | Passive | Marketed |
| Testosterone | Passive | Marketed |
| Lidocaine | Iontophoresis | Marketed |
| Epinephrine | Iontophoresis | Research |
| Corticosteroids | Iontophoresis | Research |
| Pilocarpine | Iontophoresis | Marketed; cystic fibrosis diagnosis |
| Nafarelin | Iontophoresis | Research; Pharm Res 13, 798 |
| Leuprolide | Iontophoresis | Research; J. Control. Release 31, 41 |
| Vasopressin | Iontophoresis | Research |
| Salmon calcitonin | Iontophoresis | Research; Pharm. Res. 14, 63 |
| Insulin | Iontophoresis | Research; Electrically Assisted Transdermal & Topical Drug Delivery 1998 |
| LHRH | Iontophoresis | Research; J. Phar. Sci. 87, 462 |
| Parathyroid hormone | Iontophoresis | Research |
| Desmopressin | Iontophoresis | Research; Biol. Pharm. Bull. 21, 268 |
| δ-sleep-inducing peptide | Iontophoresis | Research; Drug. Dev. Ind. Pharm. 24, 431 |

Excipients and Matrix Materials

The drug can be dispersed in a matrix material, to further control the rate of release of drug. This matrix material can be a "release system," as described in U.S. Pat. No. 5,797,898, the degradation, dissolution, or diffusion properties of which can provide a method for controlling the release rate of the chemical molecules.

The release system may provide a temporally modulated release profile (e.g., pulsatile release) when time variation in plasma levels is desired or a more continuous or consistent release profile when a constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e., pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release). The active release systems described herein can be used alone or on combination with passive release systems, for example, as described in U.S. Pat. No. 5,797,898. For example, the reservoir cap can be removed by active means to expose a passive release system, or a given substrate can include both passive and active release reservoirs.

In one embodiment, the drug formulation within a reservoir comprises layers of drug and non-drug material. After the active release mechanism has exposed the reservoir contents, the multiple layers provide multiple pulses of drug release due to intervening layers of non-drug. In another variation, the same layering system could be used in device operating by passive release.

The pharmaceutical agent can be formulated with one or more pharmaceutically acceptable excipients. Representative examples include bulking agents, wetting agents, stabilizers, crystal growth inhibitors, antioxidants, antimicrobials, preservatives, buffering agents (e.g., acids, bases), surfactants, desiccants, dispersants, osmotic agents, binders (e.g., starch, gelatin), disintegrants (e.g., celluloses), glidants (e.g., talc), diluents (e.g., lactose, dicalcium phosphate), color agents, lubricants (e.g., magnesium stearate, hydrogenated vegetable oils) and combinations thereof. In some embodiments, the excipient is a wax or a polymer. In one embodiment, the polymer comprises polyethylene glycol (PEG), e.g., typically one having a molecular weight between about 100 and 10,000 Daltons (e.g., PEG 200, PEG 1450). In another embodiment, the polymer comprises poly lactic acid (PLA), poly glycolic acid (PGA), copolymers thereof (PLGA), or ethyl-vinyl acetate (EVA) polymers. In yet another embodiment, the excipient material comprises a pharmaceutically acceptable oil (e.g., sesame oil).

In one embodiment, the excipient material includes a saturated drug solution. That is, the excipient material comprises a liquid solution formed of the drug dissolved in a solvent for the drug. The solution is saturated so that the solvent does not dissolve the solid matrix form of the drug. The saturated solution acts as a non-solvent excipient material, substantially filling pores and voids in the solid matrix.

In another embodiment, the excipient material comprises a pharmaceutically-acceptable perhalohydrocarbon or unsubstituted saturated hydrocarbon. See, for example, U.S. Pat. No. 6,264,990 to Knepp et al., which describes anhydrous, aprotic, hydrophobic, non-polar liquids, such as biocompatible perhalohydrocarbons or unsubstituted saturated hydrocarbons, such as perfluorodecalin, perflurobutylamine, perfluorotripropylamine, perfluoro-N-methyldecahydroquindine, perfluoro-octohydro quinolidine, perfluoro-N-cyclohexylpyrilidine, perfluoro-N,N-dimethylcyclohexyl methylamine, perfluoro-dimethyl-adamantane, perfluorotri-methylbicyclo (3.3.1) nonane, bis(perfluorohexyl) ethene, bis(perfluorobutyl) ethene, perfluoro-1-butyl-2-hexyl ethene, tetradecane, methoxyflurane and mineral oil.).

In one embodiment, the pharmaceutically acceptable excipient material comprises dimethyl sulfoxide (DMSO), glycerol, or ethanol.

In certain embodiments, the excipient material can be one that would not ordinarily be considered as ingredient in a dosage form. Where the implantable drug delivery device comprises one or more discrete reservoirs of small volume, e.g., microreservoirs, then it may be desirable to use organic solvents that are not possible to use in large amounts, for example due to toxicity concerns. In various embodiments, the solvents listed in Table 2 can be used as the excipient material if the device reservoir volumes are small enough to ensure that the daily exposure to the excipient cannot exceed predetermined limits, for example described in ICH Guideline Q3C: Impurities: Residual Solvents.

TABLE 2

Excipient Materials and Exposure Limits

| Excipient | Daily limit (mg) | Excipient | Daily limit (mg) |
|---|---|---|---|
| Benzene | 0.02 | 1,1,2-Trichloroethene | 0.8 |
| Carbon tetrachloride | 0.04 | Xylene | 21.7 |
| 1,2-Dichloroethane | 0.05 | Acetic acid | 50 |
| 1,1-Dichloroethene | 0.08 | Acetone | 50 |
| 1,1,1-Trichloroethane | 15 | Anisole | 50 |
| Acetonitrile | 4.1 | 1-Butanol | 50 |
| Chlorobenzene | 3.6 | 2-Butanol | 50 |
| Chloroform | 0.6 | Butyl acetate | 50 |
| Cyclohexane | 38.8 | tert-Butylmethyl ether | 50 |
| 1,2-Dichloroethene | 18.7 | Cumene | 50 |
| Dichloromethane | 6.0 | Dimethyl sulfoxide | 50 |
| 1,2-Dimethoxyethane | 1.0 | Ethanol | 50 |
| N,N-Dimethylacetamide | 10.9 | Ethyl acetate | 50 |
| N,N-Dimethylformamide | 8.8 | Ethyl ether | 50 |
| 1,4-Dioxane | 3.8 | Ethyl formate | 50 |
| 2-Ethoxyethanol | 1.6 | Formic acid | 50 |
| Ethyleneglycol | 6.2 | Heptane | 50 |
| Formamide | 2.2 | Isobutyl acetate | 50 |
| Hexane | 2.9 | Isopropyl acetate | 50 |
| Methanol | 30.0 | Methyl acetate | 50 |
| 2-Methoxyethanol | 0.5 | 3-Methyl-1-butanol | 50 |
| Methylbutyl ketone | 0.5 | Methylethyl ketone | 50 |
| Methylcyclohexane | 11.8 | Methylisobutyl ketone | 50 |
| N-Methylpyrrolidone | 5.3 | 2-Methyl-1-propanol | 50 |
| Nitromethane | 0.5 | Pentane | 50 |
| Pyridine | 2.0 | 1-Pentanol | 50 |
| Sulfolane | 1.6 | 1-Propanol | 50 |
| Tetrahydrofuran | 7.2 | 2-Propanol | 50 |
| Tetralin | 1.0 | Propyl acetate | 50 |
| Toluene | 8.9 | | |

Reservoir Caps/Control Means

The device includes structural components for controlling the time at which release of the pharmaceutical agent from the reservoir is initiated. These components include reservoir caps and reservoir control means. In one embodiment, the control means includes control circuitry, which includes the hardware, electrical components, and software needed to control and deliver electric energy from a power source to selected reservoir(s) for actuation, e.g., reservoir opening.

Reservoir Caps

As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. See, e.g., U.S. Patent Application Publication Nos. 2002/0183721 A1, which is incorporated herein by reference. Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" includes degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, as described in U.S. Patent Application Publication No. 2004/0121486 A1 to Uhland et al., which is incorporated herein by reference in its entirety.

In one embodiment, the reservoir cap is a thin metal film and is impermeable to the surrounding environment (e.g., body fluids or another chloride containing solution). In one variation, a particular electric potential is applied to the metal reservoir cap, which is then oxidized and disintegrated by an electrochemical reaction, to release the drug from the reservoir. Examples of suitable reservoir cap materials include gold, silver, copper, and zinc.

In another variation, the reservoir cap is heated (e.g., using resistive heating) to cause the reservoir cap to melt and be displaced from the reservoir to open it. See U.S. Pat. No. 6,527,762, which is incorporated herein by reference. This latter variation could be used, for example, with reservoir caps formed of a metal or a non-metal material, e.g., a polymer. In yet another variation, the reservoir cap is formed of a polymer or other material that undergoes a temperature-dependent change in permeability such that upon heating to a pre-selected temperature, the reservoir is rendered permeable to the drug and bodily fluids to permit the drug to be released from the reservoir through the reservoir cap.

In still another embodiment, the reservoir cap is formed of a conductive material, such as a metal film, through which an electrical current can be passed to electrothermally ablate it, as described in U.S. Patent Application Publication No. 2004/0121486 A1 to Uhland et al. Representative examples of suitable reservoir cap materials include gold, copper, aluminum, silver, platinum, titanium, palladium, various alloys (e.g., Au—Si, Au—Ge, Pt—Ir, Ni—Ti, Pt—Si, SS 304, SS 316), and silicon doped with an impurity to modulate the conductivity/resistivity because one can use the impurity to increase or decrease the conductivity or resistivity of the silicon, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e., electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated and ruptured. In this embodiment, the reservoir cap is formed of an electrically conductive material and the control circuitry comprises an electrical input lead connected to said reservoir cap, an electrical output lead connected to said reservoir cap, wherein the reservoir cap is ruptured by application of an electrical current through the reservoir cap via the input lead and output lead. Preferably, the control circuitry further comprises a source of electric power for applying the electrical current.

In yet another embodiment, the reservoir opening is closed by a reservoir cap comprising a dielectric or ceramic film layer and the actuation means comprises (i) a electrically conductive (e.g., metal) layer on top of the dielectric or ceramic film layer, and (ii) power source and control circuitry for delivering an electric current through the electrically conductive layer in an amount effective to rupture the dielectric or ceramic film layer, wherein the rupture is due to thermal expansion-induces stress on the dielectric or ceramic film layer. The electrically conductive layer and the actuation means can be designed thermally ablate the electrically conductive layer or the electrically conductive layer could remain, in whole or in part, after rupturing the dielectric or ceramic film layer, depending on the particular design for opening/actuation the release of drug from the reservoir.

In passive release devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes. Characteristics can be different for each reservoir cap to provide different times of release of drug formulation. For example, any combination of polymer, degree of crosslinking, or polymer thickness can be modified to obtain a specific release time or rate.

A combination of passive and/or active release reservoir cap can be present in a single delivery device. For example, the reservoir cap can be removed by electrothermal ablation to expose a passive release system that only begins its passive release after the reservoir cap has been actively removed. Alternatively, a given device can include both passive and active release reservoirs.

In still another embodiment, release can be controlled from the substrate reservoirs using passive control means, such as a biodegradable matrix material or layering of drug material with non-drug material, without the use of reservoir caps. In one variation of this "no cap" approach, reservoir caps are provided prior to device use, i.e., prior to application of (adhering) the device to the skin, and then immediately before application to the skin all of these reservoir caps are (manually) removed. For instance, these caps could be part of a protective layer that is removed just prior to adhering the patch to the skin.

In one embodiment, each reservoir includes a single, discrete reservoir cap, covering a single opening that can be opened. In another embodiment, each reservoir includes two or more openings that can be covered by two or more discrete reservoir caps, where each reservoir cap can, but need not, be independently disintegrated to open the reservoir. There can be a one-to-one correspondence between the number of reservoir openings and the number of reservoir caps; however, in various embodiments, it is possible that a single discrete reservoir can cover more than one reservoir opening.

Control Means

Figure 4:
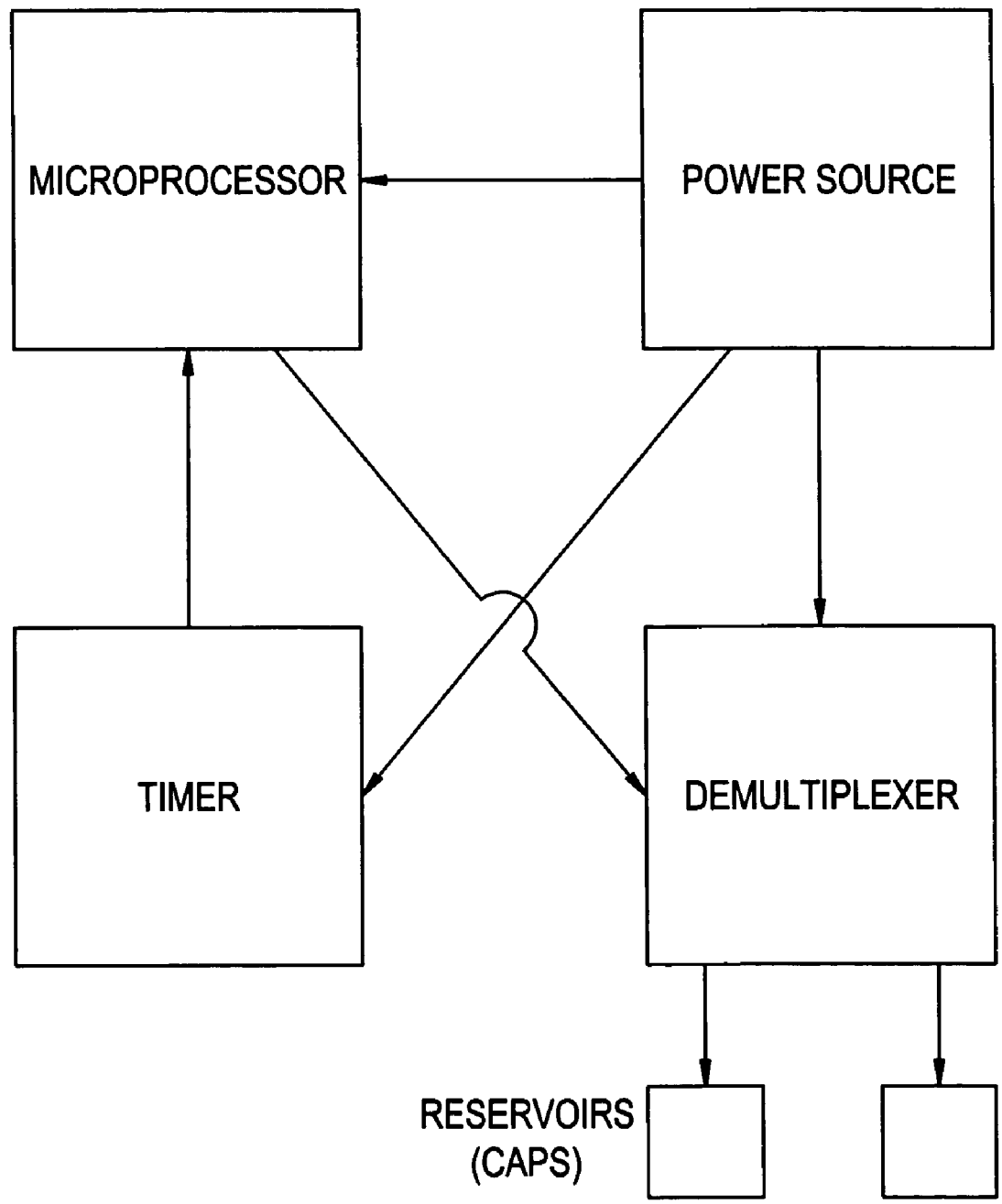
FIG. 4 is a schematic of the operation of one embodiment of the control means for the medical device for transdermal drug delivery or analyte sensing described herein.

The reservoir control means can provide intermittent or effectively continuous release of the drug formulation. The particular features of the control means depend on the mechanism of reservoir cap activation described herein. For example, the control means can include an input source, a microprocessor, a timer, a demultiplexer (or multiplexer), and a power source. The power source provides energy to activate the selected reservoir, e.g., to trigger release of the drug formulation from the particular reservoir desired for a given dose. See FIG. 4. For example, the operation of the reservoir opening system can be controlled by an on-board microprocessor. The microprocessor can be programmed to initiate the disintegration or permeabilization of the reservoir cap at a pre-selected time or in response to one or more of signals or measured parameters, including receipt of a signal from another device (for example by remote control or wireless methods) or detection of a particular condition using a sensor such as a biosensor. In another embodiment, a simple state machine is used, as it typically is simpler, smaller, and/or uses less power than a microprocessor. The device can also be activated or powered using wireless means, for example, as described in U.S. 2002/0072784 A1 to Sheppard et al., which is incorporated herein by reference.

In one embodiment, the device includes a substrate having a two-dimensional array of reservoirs arranged therein, a drug formulation contained in the reservoirs, anode reservoir caps covering a semi-permeable membrane for each of the reservoirs, cathodes positioned on the substrate near the anodes, and means for actively controlling disintegration of the reservoir caps. The means includes a power source and circuitry to control and deliver an electrical potential; the energy drives a reaction between selected anodes and cathodes. Upon application of a potential between the electrodes, electrons pass from the anode to the cathode through the external circuit causing the anode material (reservoir cap) to oxidize and dissolve into the surrounding fluids, exposing and releasing the drug formulation. The microprocessor directs power to specific electrode pairs through a demultiplexer as directed by an EPROM, remote control, or biosensor.

In another embodiment, the activation energy initiates a thermally driven rupturing or permeabilization process, for example, as described in U.S. Pat. No. 6,527,762. For example, the means for controlling release can actively disintegrate or permeabilize a reservoir cap using a resistive heater. The resistive heater can cause the reservoir cap to undergo a phase change or fracture, for example, as a result of thermal expansion of the reservoir cap or release system, thereby rupturing the reservoir cap and releasing the drug from the selected reservoir. The application of electric current to the resistor can be delivered and controlled using components as described above for use in the electrochemical disintegration embodiment. For example, a microprocessor can direct current to select reservoirs at desired intervals.

In a preferred embodiment, control means controls electrothermal ablation of the reservoir cap. For example, the drug delivery device could include a reservoir cap formed of an electrically conductive material; an electrical input lead connected to the reservoir cap; an electrical output lead connected to the reservoir cap; and a control means to deliver an effective amount of electrical current through the reservoir cap, via the input lead and output lead, to locally heat and rupture the reservoir cap, for example to release the drug formulation or expose the sensor located therein. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed as described in U.S. Patent Application Publication No. 2004/0121486 A1 to Uhland et al.

In one embodiment, the control means includes a microprocessor, a timer, a demultiplexer (or multiplexer), and an input source (for example, a memory source, a signal receiver, or a biosensor), and a power source. The timer and demultiplexer circuitry can be designed and incorporated directly onto the surface of the microchip during electrode fabrication, or may be incorporated in a separate microchip. The microprocessor translates the output from memory sources, signal receivers, or biosensors into an address for the direction of power through the demultiplexer to a specific reservoir on the device. Selection of a source of input to the microprocessor such as memory sources, signal receivers, or biosensors depends on the microchip device's particular application and whether device operation is preprogrammed, controlled by remote means, or controlled by feedback from its environment (i.e., biofeedback). For example, a microprocessor can be used in conjunction with a source of memory such as erasable programmable read only memory (EPROM), a timer, a demultiplexer, and a power source such as a battery or a biofuel cell. A programmed sequence of events including the time a reservoir is to be opened and the location or address of the reservoir is stored into the EPROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor. In another embodiment, the electronics are included on the substrate/chip itself, for example, where the electronics are based on diode or transistor technology known in the art.

In one preferred embodiment, the electronics are separable from the transdermal drug delivery device, such that they are reusable with multiple transdermal drug delivery devices. One example of such a system is shown in FIG. 2. The cost to use a transdermal system like this would be significantly less than a system where the electronics were not separable and only could be used once.

Other methods and multi-reservoir devices for controlled release of drug are described in U.S. Patent Application Publications Nos. 2002/0072784 A1, 2002/0099359 A1, 2002/0187260 A1, 2003/0010808 A1, 2004/0082937 A1, 2004/016914 A1; and U.S. Pat. No. 6,808,522, No. 6,730,072, No. 6,773,429, No. 6,123,861, all of which are incorporated by reference herein.

Securing Means

Essentially any device known in the art for securing objects to the skin of a human or other mammalian animal can be used. For example, the securing means can include one or more biocompatible adhesives, straps, or elastic bands. In one embodiment, the securing means is provided along the periphery of a housing of the device. Adhesive securing means can be, or can be readily adapted from, those known in the art for securing transdermal patches, such as those currently used in commercially available transdermal patches. See, e.g., U.S. Pat. No. 6,632,906.

In one embodiment, the adhesive is provided on a thin permeable material, such as a porous polymer layer, or a woven or non-woven fabric layer, which is adjacent the reservoir caps or the transport means. In one embodiment, the adhesive layer is permeable to the one or more pharmaceutical agents. In one embodiment, the polymer layer comprises a hydrogel.

In a preferred embodiment, the securing means comprises a pressure sensitive bioadhesive, as known in the art.

Transport Means

As used herein, "transport means" or "means for transporting" refers to any devices or materials for transferring the pharmaceutical agent that has been released from the reservoirs from the opening of the reservoir to the surface of or into the skin of the patient.

The choice of transport mechanism(s) is at least partially dependent on the drug molecule selected for delivery. Generally, these delivery mechanisms are characterized as follows: (1) passive, (2) chemical penetration enhancers, (3) ultrasonography, (4) iontophoresis, (5) electroosmosis, (6) electroporation, (7) heat, and (8) microneedles. For passive mechanisms, a therapeutic dose is achievable without enhancement because of high potency and desirable physiochemical characteristics, which is typically associated with small lipophilic molecules. Chemical penetration enhancers can be added to the drug formulation to increase flux through the skin or mucosal surface. Examples include phosphate buffered saline, PEG 200 dilaurate, isopropyl myristate, glycerol trioleate, 50% ethanol/50% phosphate buffered saline, linoleic acid in 1/1 ethanol/phosphate buffered saline. With ultrasonography, low-frequency ultrasound is applied prior to or simultaneously with drug delivery, particularly for low- and high-molecular weight drugs. With iontophoresis, a continuous low current is applied to enhance delivery of a charged molecular species. With electroosmosis, enhancement is by entrainment of bulk liquid by charged ions moving in an electric field, which can be used to deliver neutral and charged species. Electroporation utilizes a high voltage pulse to help deliver large (proteins, oligonucleotides) and small molecules. Heat is another mechanism, where controlled exothermic reaction is used to generate heat to drive transport across skin. Microneedles, which are used to create pathways through the stratum corneum, can take a variety of forms, including an array of titanium microprojections, such as the MACROFLUX™ (Alza Corp.).

The device can include, or be used with, devices and means for application of acoustic energy (see, e.g., U.S. Patent Application Publication No. 2002/0082527 A1; U.S. Patent Application Publication No. 2002/0045850 A1), sonophoresis/ultrasound (see, e.g., U.S. Pat. Nos. 6,620,123, 6,491,657), electroporation, iontophoresis (see, e.g., U.S. Pat. Nos. 6,629,968, 6,377,847, U.S. Patent Application Publication No. 2001/0056255 A1), heat (see, e.g., U.S. Pat. Nos. 6,756,053, 6,488,959) or other means known in the art for enhancing transdermal administration of drugs or transdermal diagnostics (e.g., glucose sensing).

In one embodiment, the transport means comprises a transport medium reservoir disposed between the reservoir caps and the skin. For example, the transport medium can include a permeable body through which the one or more pharmaceutical agents can diffuse following their release from the reservoir, or through which an analyte from the patient's skin can diffuse toward sensors disposed in the reservoirs. The transport medium can comprise a reservoir containing a liquid, gel, or semi-solid permeation material (also referred to in the art as a rate-limiting membrane). Representative examples of suitable permeation materials include various polymers and hydrogels known in the art, which preferably are non-reactive with the drug formulation or skin.

In one embodiment, the transport means includes one or more permeation enhancers, as for example, described in U.S. Pat. No. 6,673,363, which is incorporated herein by reference.

In one embodiment, the means for transporting comprises one or more microneedles. Examples of microneedles suitable for transdermal drug delivery and analyte sensing are described in U.S. Pat. Nos. 6,743,211, 6,661,707, 6,503,231, and 6,334,856, all to Prausnitz et al., and in U.S. Pat. Nos. 6,230,051 and 6,219,574, both to Cormier et al.

In one embodiment, the device includes positive displacement mechanisms for driving the one or more pharmaceutical agents out of the reservoirs. In one embodiment, an osmotic pressure generating material or other swellable material drives a piston to force a drug formulation out of the reservoir. In another embodiment, the device includes features for the positive displacement and/or accelerated release techniques described in U.S. Patent Application Publication No. 2004/0106914 to Coppeta et al.

Illustrative Embodiments

Figure 5:
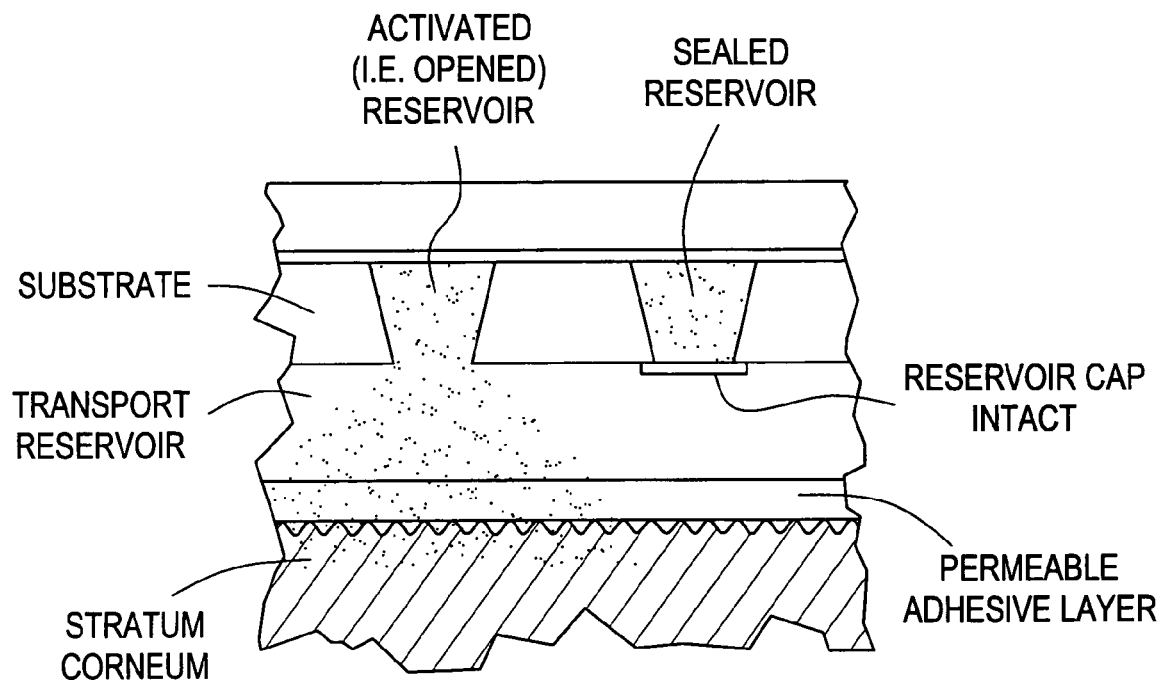
FIG. 5 is a cross-sectional view of one portion of one embodiment of the device shown in FIG. 1, showing one reservoir pre-actuation and one reservoir post-actuation.

In one embodiment, the transdermal device includes a patch comprising a secondary reservoir for receiving the drug released from each reservoir in the substrate. The secondary reservoir may be a single pool into which the dose is diluted, or the pool space may be divided into individual channels for delivery of each dose with minimal dilution. Upon release from the substrate reservoir, the drug diffuses into and through the secondary reservoir and then out of the patch and into the patient's skin. See FIG. 5. In an alternative embodiment (not shown) the secondary reservoir is replaced with a layer of substrate that has media-filled holes with spacing corresponding to reservoir membrane openings, which allows release of reservoir contents without dilution. In one embodiment, the device includes a rigid or flexible housing that contains the substrate, as well as the control means and power source. When the drug enters the secondary reservoir, it may distribute itself homogeneously throughout the secondary reservoir, such that diffusion is substantially uniform across the entire surface area interfacing the skin. The secondary reservoir optionally can include a permeable or semi-permeable adhesive layer at this interface.

FIG. 1 shows device 10 which includes substrate 12 having reservoirs 14 which contain one or more pharmaceutical agents. The device 10 further includes fluid reservoir 16 and a permeable adhesive layer 18 for securing the device to the patient's skin. The device 10 further includes microprocessor-based or remote control means 20 and battery or other power supply 22. Preferably, the portion of the device comprising the control mans and power supply is flexible. The device includes an optional housing or outer covering 24. In an alternative embodiment (not shown) fluid reservoir 16 is replaced with a layer of substrate that has media-filled holes with spacing corresponding to reservoir membrane openings, which allows release of reservoir contents without dilution.

Figure 6:
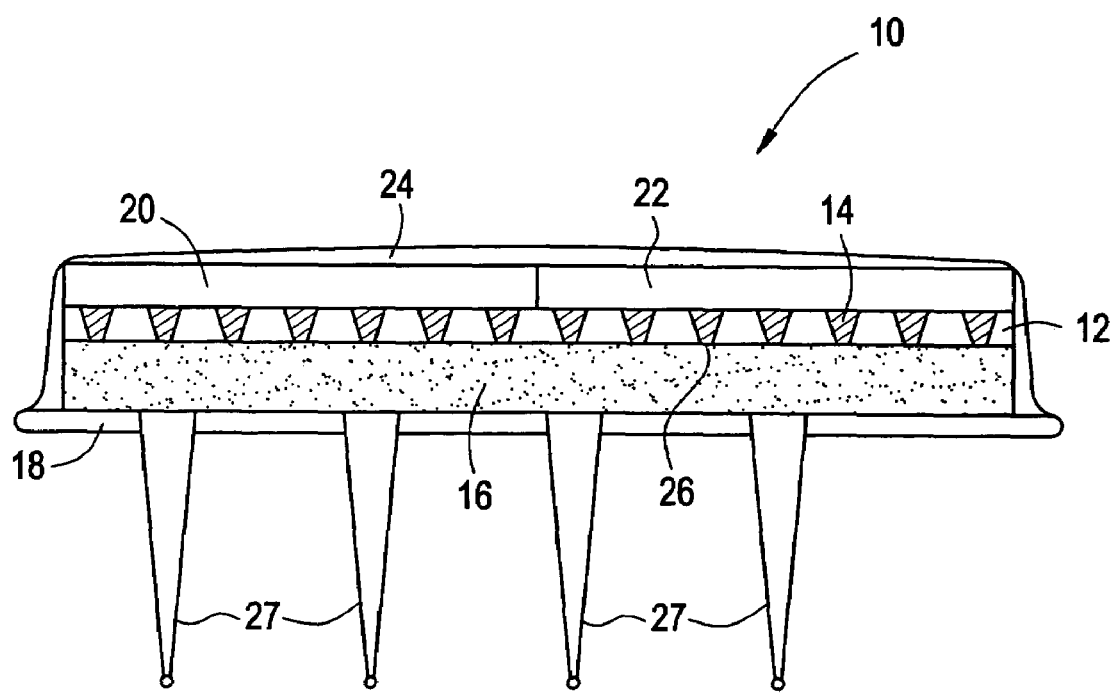
FIG. 6 is a cross-sectional view of one embodiment of the medical device for transdermal drug delivery or analyte sensing that includes microneedles.

FIG. 6 shows an alternate version of device 10, wherein the means for transporting further comprises a plurality of microneedles 27, which may be solid, hollow, or porous. For example, U.S. Pat. No. 6,230,051 to Cormier et al. (Alza Corporation) discloses needle-like protrusions, barbs, or blades that puncture the stratum corneum, and diffusion of drug proceeds along the pathway between the outer surface of the needle and the skin/tissue circumscribing the needle. In an alternative embodiment, the fluid reservoir is replaced with a layer of substrate that has media-filled holes with spacing corresponding to reservoir membrane openings, which allows release of reservoir contents without dilution. That is, the microneedles can be spaced to match the reservoir openings. In use, one can apply the solid microneedles first, then remove them, and then apply the drug delivery patch, or one can use hollow microneedles matched to the spacing of the reservoir openings attached to the patch.

Figure 2A:
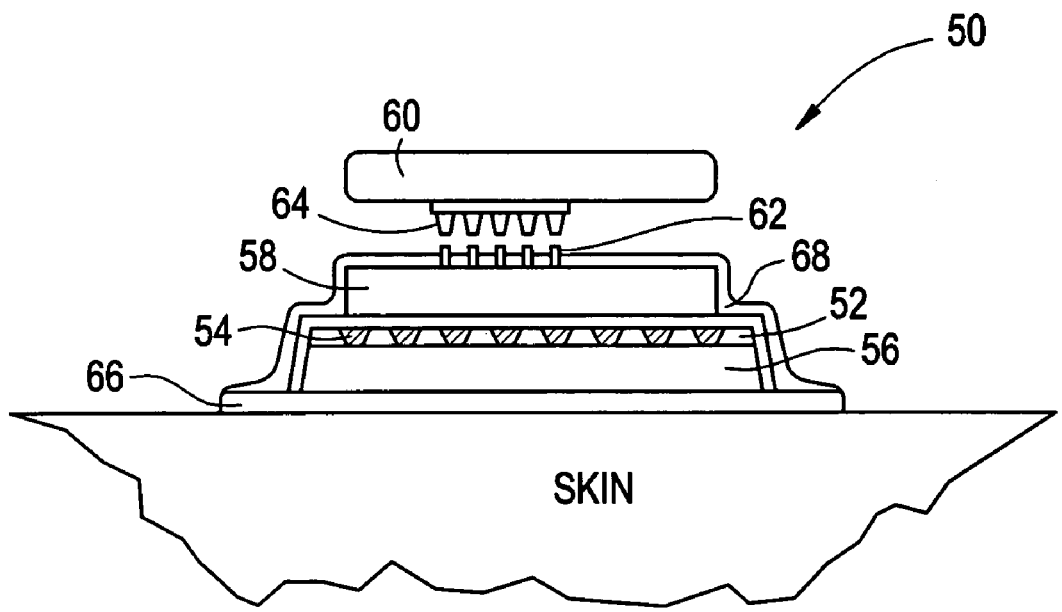
FIGS. 2A and 2B are a perspective view (FIG. 2A) and a cross-sectional view (FIG. 2B) of another embodiment of the medical device for transdermal drug delivery or analyte sensing described herein.
Figure 2B:
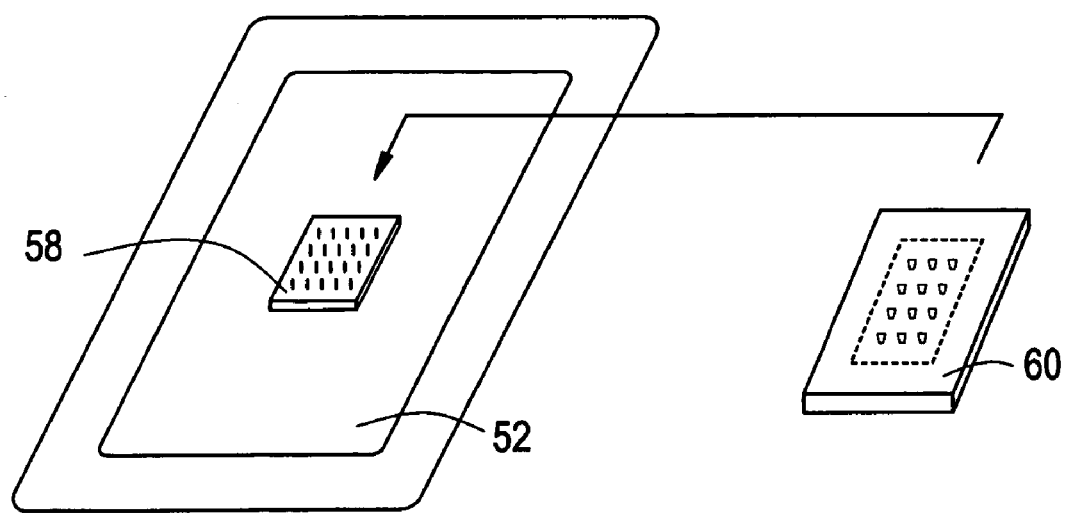

The device electronics optionally can be located in a separate package. In one embodiment, the device includes a removably attachable electronics portion that comprises the power source and at least a portion of the control circuitry. This electronics portion can be re-used many times and can be re-programmed wirelessly, which advantageously could improve cost effectiveness. One embodiment of such a device is illustrated in FIGS. 2A-B. These Figures show device 50 which includes substrate 52 having reservoirs 54 which contain the drug. The device 50 further includes fluid reservoir 56 and an adhesive layer 66 for securing the device to the patient's skin. The control means for selective releasing the drug includes an electronics interface portion 58, and removable power and electronics portion 60. The removable power and electronics portion 60 and the electronics interface portion 58 are can be selectively attached together by matingly engaging male connector posts 62 with female receptacles 64. The device is sealed or packaged in a protective material 68. For example, the protective material can be a polymeric coating or laminate composite structure. In an alternative embodiment (not shown) fluid reservoir 56 is replaced with a layer of substrate that has media-filled holes with spacing corresponding to reservoir membrane openings, which allows release of reservoir contents without dilution.

Figure 3:
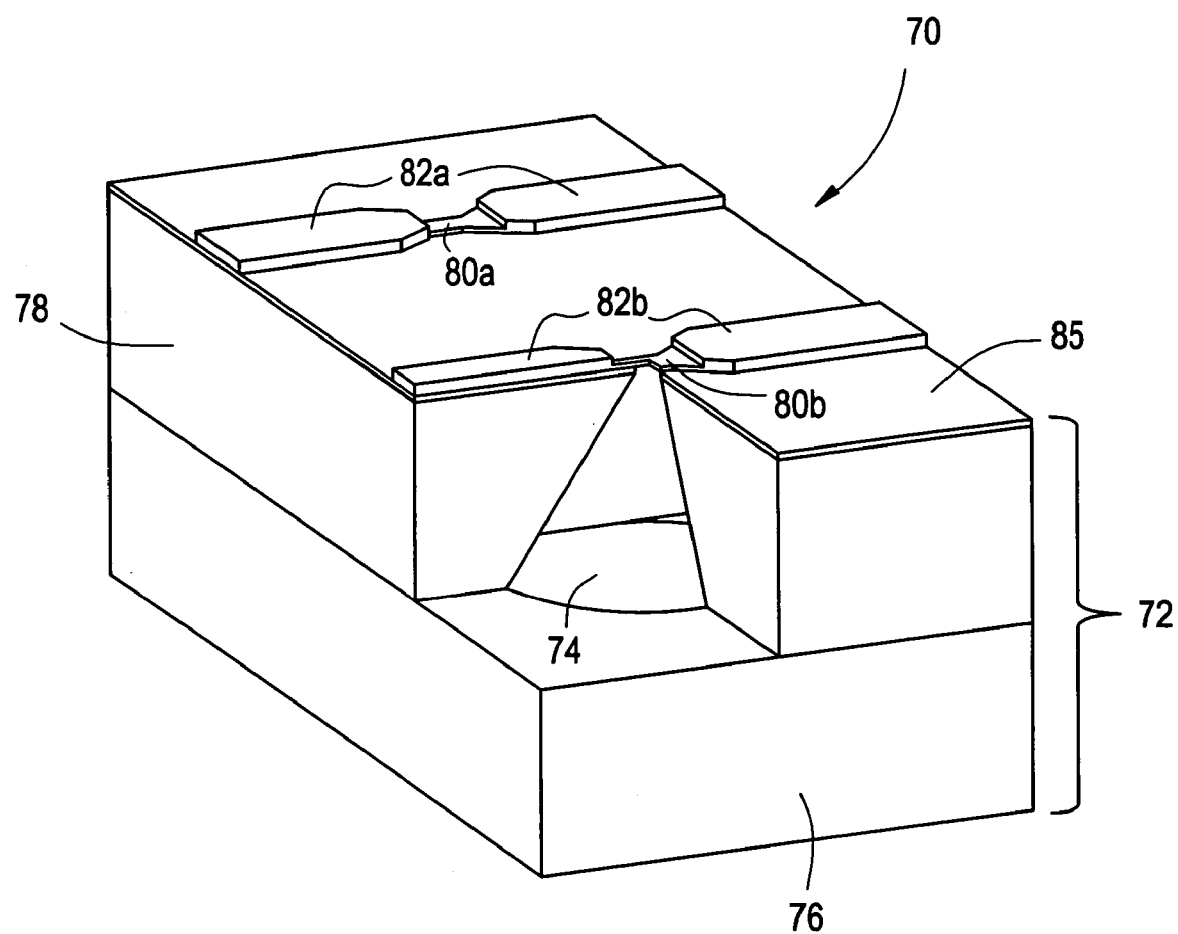
FIG. 3 is a perspective, cross-sectional view of one embodiment of the reservoir and body portion of the drug delivery or sensing device described herein.

FIG. 3 shows device 70 (shown only in part) which comprises body portion 72, which includes a first substrate portion 78 and a second substrate portion 76. Reservoirs 74 are defined in the body portion. (Two are located in the body portion in this illustration, but only one can be seen from the cut-away of part of the first substrate portion.) The release opening of the reservoirs are covered by reservoir caps 80*a* and 80*b*. Metal conductors 82*a* and 82*b* are electrically connected to the reservoir caps, for delivering electric current to the reservoir caps. Dielectric layer 85 is provided on the outer surface of the first substrate portion and is underneath the conductors.

Use of the Medical Device

In preferred embodiments, the device can be used to delivery a wide variety of drugs or drug combinations to a patient in need thereof. The device can be tailored to delivery the drug or drugs over an extended period of time, with a range of controlled release profiles, for example, to provide a relatively constant or a varied plasma drug levels. The device may be removed periodically, provided it does not undesirably interrupt delivery of the drug. The drug formulation and device may also be tailored for systemic (bioavailability goal 100%) or topical (bioavailability goal 0%) delivery.

In one embodiment, the medical device is used for transdermal delivery of parathyroid hormone (PTH). PTH is released from the reservoirs in a manner to intermittently deliver a pharmaceutically effective amount of the PTH through the skin for systemic administration. The delivery optionally can be facilitated by one or more transport acceleration means as described above.

Other applications include the delivery of pain medications. Examples include lidocaine, for needle sticks, IV insertion, or other dermatological procedures, or the delivery of more potent pain medications, such as fentanyl, for greater pain relief, such as for treating breakthrough pain in cancer patients. In still other applications, the devices can be used to deliver drugs for joint pain, anti-emetic applications, migraine treatments, fertility treatments, and Parkinson's medications.

In still other applications, the device is used in sensing applications. For example, the micro-reservoirs could contain sensors for measuring an analyte that can be drawn from the skin. Alternatively, the device could operate not remove fluid but, rather, to place small quantities of solution containing low concentrations of Small Molecule Metabolite Reporters (SMMRs) into the skin for direct reading of the SMMR fluorescence spectral characteristics as an indication of both epidermal skin and blood glucose levels, as known in the art.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A medical device for transdermal administration of one or more pharmaceutical agents to a patient in need thereof comprising:
   a substrate;
   a plurality of discrete reservoirs in the substrate;
   one or more pharmaceutical agents stored in the reservoirs;
   discrete reservoir caps which prevent the one or more pharmaceutical agents from passing out from the reservoirs;
   control means for actuating release of the one or more pharmaceutical agents from one or more of the reservoirs by disintegrating or permeabilizing the reservoir caps;
   means for securing the device to the skin of the patient; and
   means for transporting the one or more pharmaceutical agents to the skin following release from the one or more reservoirs, wherein the means for transporting comprises a flexible or rigid member having media-filled holes with spacing corresponding to openings in said reservoirs, which allows release of reservoir contents without dilution.

2. The device of claim 1, wherein the reservoir cap is formed of an electrically conductive material and the control means comprises an electrical input lead connected to said reservoir cap, an electrical output lead connected to said reservoir cap, wherein the reservoir cap is ruptured by application of an electrical current through the reservoir cap via the input lead and output lead.

3. The device of claim 2, further comprising a source of electric power for applying the electrical current.

4. The device of claim 1, wherein the reservoir cap comprises a metal film.

5. The device of claim 1, wherein the means for securing comprises a pressure sensitive adhesive.

6. The device of claim 1, wherein the means for securing comprises an adhesive layer which is permeable to the one or more pharmaceutical agents.

7. The device of claim 1, wherein the media of said media-filled holes is a transport medium which comprises a liquid, gel, or semi-solid permeation material.

8. The device of claim 1, further comprising a housing which contains the substrate, control means, and a power source.

9. The device of claim 1, further comprising a removably attachable electronics portion which comprises the power source and at least a portion of the control means.

10. The device of claim 1, wherein the means for transporting further comprises a plurality of microneedles.

11. The device of claim 1, wherein the means for transporting further comprises one or more chemical penetration enhancers.

12. The device of claim 1, wherein the means for transporting further comprises an ultrasound generator.

13. The device of claim 1, wherein the means for transporting further comprises means for effecting iontophoresis, electroosmosis, or electroporation.

14. The device of claim 1, wherein the means for transporting further comprises a heating element.

15. The device of claim 1, wherein the reservoirs are microreservoirs.

16. The device of claim 1, wherein the one or more pharmaceutical agents comprises a drug selected from the group consisting of androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, anti-obesity agents, nicotine, testosterone, estradiol, nitroglycerin, clonidine, dexamethasone, wintergreen oil, tetracaine, lidocaine, fentanyl, sufentanil, progestrone, insulin, Vitamin A, Vitamin C, Vitamin B, prilocaine, bupivacaine, sumatriptan, dihydroergotamine, and combinations thereof.

17. A medical device for transdermal administration of one or more pharmaceutical agents to a patient in need thereof comprising:
   a substrate;
   a plurality of discrete reservoirs in the substrate;
   one or more pharmaceutical agents stored in the reservoirs;
   discrete reservoir caps which prevent the one or more pharmaceutical agents from passing out from the reservoirs;
   control means for actuating release of the one or more pharmaceutical agents from one or more of the reservoirs by disintegrating or permeabilizing the reservoir caps;
   an adhesive or strap material for securing the device to the skin of the patient; and
   a body defining a transport medium reservoir disposed between the reservoir caps and the skin of the patient, the body and reservoir facilitating transport of the one or more pharmaceutical agents to the skin following their release from the one or more reservoirs, wherein the transport medium reservoir comprises a single pool of a biocompatible transport fluid into which the one or more pharmaceutical agents are diluted prior to delivery to the skin.

18. The device of claim 17, wherein the transport medium reservoir contains a liquid, gel, or semi-solid permeation material.

19. The device of claim 17, wherein the reservoir cap is formed of an electrically conductive material and the control means comprises a source of electric power and an electrical input lead connected to said reservoir cap, an electrical output lead connected to said reservoir cap, wherein the reservoir cap is ruptured by application of an electrical current through the reservoir cap via the input lead and output lead.

20. The device of claim 19, further comprising a housing which contains the substrate and control means.

21. The device of claim 19, wherein the power source and at least a portion of the control means are provided in a removably attachable electronics portion.

22. The device of claim 17, wherein the reservoir cap comprises a metal film.

23. The device of claim 17, wherein said adhesive is a pressure sensitive adhesive.

24. The device of claim 17, wherein said adhesive is permeable to the one or more pharmaceutical agents.

25. The device of claim 17, wherein said body comprises a plurality of microneedles.

26. The device of claim 17, wherein said biocompatible transport fluid comprises one or more chemical penetration enhancers.

27. The device of claim 17, further comprising an ultrasound generator or means for effecting Iontophoresis, electroosmosis, or electroporation.

28. The device of claim 17, further comprising a heating element for generating heat to drive transport of the one or more pharmaceutical agents across the skin.

29. The device of claim 17, wherein the reservoirs are microreservoirs.

30. The device of claim 17, wherein the one or more pharmaceutical agents comprises a drug selected from the group consisting of androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, anti-obesity agents, nicotine, testosterone, estradiol, nitroglycerin, clonidine, dexamethasone, wintergreen oil, tetracaine, lidocaine, fentanyl, sufentanil, progestrone, insulin, Vitamin A, Vitamin C, Vitamin E, prilocaine, bupivacaine, sumatriptan, dihydroergotamine, and combinations thereof.

\* \* \* \* \*